(12) United States Patent
Hamaji et al.

(10) Patent No.: US 8,734,779 B2
(45) Date of Patent: May 27, 2014

(54) 5-FLUOROURACIL-RESISTANT BACTERIA AND METHOD FOR PRODUCTION THEREOF

(75) Inventors: Yoshinori Hamaji, Kobe (JP); Minoru Fujimori, Matsumoto (JP); Jun Amano, Matsumoto (JP); Shun'ichiro Taniguchi, Matsumoto (JP)

(73) Assignee: Anaeropharma Science Inc., Tokyo (JP)

( * ) Notice: Subject to any disclaimer, the term of this patent is extended or adjusted under 35 U.S.C. 154(b) by 1481 days.

(21) Appl. No.: 11/910,880

(22) PCT Filed: Apr. 4, 2006

(86) PCT No.: PCT/JP2006/307102
§ 371 (c)(1),
(2), (4) Date: Dec. 18, 2007

(87) PCT Pub. No.: WO2006/109619
PCT Pub. Date: Oct. 19, 2006

(65) Prior Publication Data
US 2009/0280091 A1 Nov. 12, 2009

(30) Foreign Application Priority Data
Apr. 8, 2005 (JP) ................. 2005-112557

(51) Int. Cl.
*A61K 48/00* (2006.01)
*C12Q 1/68* (2006.01)
*C12P 21/06* (2006.01)
*C12N 1/20* (2006.01)
*C12N 15/00* (2006.01)
*C12N 15/74* (2006.01)
*C12N 9/78* (2006.01)
*C12N 9/88* (2006.01)
*C12N 9/14* (2006.01)
*C07H 21/04* (2006.01)

(52) U.S. Cl.
USPC ... 424/93.2; 424/93.4; 435/252.3; 435/320.1; 435/69.1; 435/6.1; 435/227; 435/195; 435/183; 536/23.2

(58) Field of Classification Search
None
See application file for complete search history.

(56) References Cited

U.S. PATENT DOCUMENTS

| | | | |
|---|---|---|---|
| 6,080,849 A | 6/2000 | Bermudes et al. | |
| 6,190,657 B1 | 2/2001 | Pawelek et al. | |
| 6,447,784 B1 | 9/2002 | Bermudes et al. | |
| 6,475,782 B1 | 11/2002 | Escobedo et al. | |
| 6,685,935 B1 | 2/2004 | Pawelek et al. | |
| 6,863,894 B2 | 3/2005 | Bermudes et al. | |
| 6,923,972 B2 | 8/2005 | Bermudes et al. | |
| 6,962,696 B1 | 11/2005 | Bermudes et al. | |
| 7,354,592 B2 | 4/2008 | Bermudes et al. | |
| 2004/0219169 A1 | 11/2004 | Bermudes et al. | |
| 2004/0229338 A1 | 11/2004 | King et al. | |
| 2005/0025745 A1 | 2/2005 | Fujimori et al. | |
| 2005/0249706 A1 | 11/2005 | Bermudes et al. | |
| 2007/0009489 A1 | 1/2007 | Bermudes et al. | |

FOREIGN PATENT DOCUMENTS

| | | |
|---|---|---|
| JP | 2002-097144 | 4/2002 |
| JP | 2004-519236 A | 7/2004 |
| WO | WO 02/068662 A1 | 9/2002 |

OTHER PUBLICATIONS

Hamaji et al. Proc Amer Assoc Cancer Res, vol. 46, Apr. 2005, Abstract #3359.*
Ballongue et al. Action sur la flore intestinale de laits fermentes au Bifidobacterium, Lait (1993) 73: 249-256 (see English Machine translation).*
U.S. Appl. No. 10/782,899, filed Feb. 23, 2004, Fujimori et al.
U.S. Appl. No. 11/718,680, filed Jun. 25, 2007, Kano et al.
International Preliminary Report on Patentability for the corresponding PCT Application No. PCT/JP2006/307102, actual completion of the Report: Oct. 9, 2007; date of mailing: Oct. 18, 2007.
Nagle, Jr. et al. "5-Fluorouracil-Resistant Strain of Methanobacterium Thermoautotrophicum," *Journal of Bacteriology*, p. 4119-4123, Sep. 1987.
International Search Report in PCT/JP2006/30712 (completed date Apr. 19, 2006; Mailing Date Apr. 25, 2006.
Cheng, et al., "Antitumor efficacy of CD/5-FC suicide gene therapy system mediated by bifidobacterium infantis against melanoma", Database Medline [Online] US Nat'l Library of Med., Mar. 2005, Absract, XP002503787.
Nakamura, et al., "Cloned cytosine deaminase gene expression of bifidobacterium longum and application to enzyme/pro-drug therapy of hypoxic solid tumors", Biosci. Biotechnol. Biochem., Jan. 1, 2002, vol. 66, No. 11, pp. 2362-2366.
King, et al., "Tumor-targeted salmonella expressing cytosine deaminase as an anticancer agent", Human Gene Ther., Jul. 1, 2002, vol. 13, pp. 1225-1233.
Theys, et al., "Specific targeting of cytosine deaminase to solid tumors by engineered clostridium acetobutylicum", Cancer Gene Ther., Apr. 1, 2001, vol. 8, No. 4, pp. 294-297.
Liu, et al., "Anticancer efficacy of systematically delivered anaerobic bacteria as gene therapy vectors targeting tumor hypoxia/necrosis", Gene Ther., Feb. 2002, vol. 9, No. 4, pp. 291-296.

(Continued)

Primary Examiner — Iqbal H Chowdhury
(74) Attorney, Agent, or Firm — Foley & Lardner LLP

(57) ABSTRACT

The present invention provides a method for producing a cytosine deaminase (CD)-expressing, 5-fluorouracil (5-FU)-resistant microorganism which can grow in anaerobic tumor tissues, can express CD, and has a resistance to 5-FU at a concentration that is at least effective for antitumor activity. More specifically, the method is a method (A) comprising performing subculture or acclimation culture of a CD-expressing microorganism which can grow in anaerobic tumor tissues, in the presence of 5-fluorocytosine (5-FC), or a method (B) comprising (1) performing subculture or acclimation culture of a microorganism which can grow in anaerobic tumor tissues and does not express CD, in the presence of 5-FU to produce a 5-FU-resistant microorganism and (2) transforming the 5-FU-resistant microorganism by introducing a CD gene. The present invention also provides the CD-expressing, 5-FU-resistant microorganism and a pharmaceutical composition comprising the microorganism.

25 Claims, 3 Drawing Sheets

(56) References Cited

OTHER PUBLICATIONS

Sasaki, et al., "Genetically engineered bifidobacterium longum for tumor-targeting enzyme-prodrug therapy of autochthonous mammary tumors in rats", Cancer Sci., Jul. 2006, vol. 97, No. 7, pp. 649-657.
Cheng, et al., "Antitumor effect of aytosine deaminase/5-fluorocytosine suicide gene therapy system mediated by bifidobacterium infantis on melanoma", Acta Pharm. Sinica, May 2005, vol. 26, No. 5, pp. 629-634.
Fujimori, et al., "Genetically engineered bifidobacterium as a drug delivery system for systemic therapy if metastatic breast cancer patients", Breast Cancer, 2006, vol. 13, No. 1, pp. 27-31.
Challa, et al., "Bifidobacterium longum and lactulose suppress azoxymethane-induced colonic aberrant crypt foci in rats", 1997, vol. 18, No. 3, pp. 517-521.
Tanaka, et al., "Structural and functional analysis of pTB6 from bifidobacterium longum", Biosci. Biotechnol. Biochem., Feb. 1, 2005, vol. 69, No. 2, pp. 422-425.
Hamaji, et al., "Strong enhancement of recombinant cytosine deaminase activity in bifidobacterium longum for tumor-targeting enzyme/prodrug therapy", Biosci. Biotechnol. Biochem., Apr. 2007, vol. 71, No. 4, pp. 874-883.
Yazawa, et al., "Bifidobacterium longum as a delivery system for gene therapy of chemically induced rat mammary tumors", Mar. 1, 2001, vol. 66, No. 2, pp. 165-170.
Li, et al., "Bifidobacterium adolescentis as a delivery system of endostatin for cancer gene therepy: Selective inhibitor of angiogenesis and hypoxic tumor growth", Cancer Gene Ther., Feb. 2003, vol. 10, No. 2, pp. 105-111.
Andersen et al., "Pyrimidine, purine and nitrogen control of cytosine deaminase synthesis in *Escherichia coli* K 12. Involvement of the *gInLG* and *purr* genes in the regulation of *coda* expression," Arch. Microbiol., 1989, 152:115-118.
Austin et al., "A First Step in the Development of Gene Therapy for Colorectal Carcinoma: Cloning, Sequencing, and Expression of *Eschericia cili* Cytosine Deaminase," Molecular Pharmacology, 1992, 43:380-387.
Davis et al., "Enzyme/prodrug gene therapy: Antitumor effects of cationic liposome-mediated delivery of the cytosine deaminase (CD) gene and 5-fluorocytosine (5-FC) administration in mice bearing NCI-H460 lung tumors," Proc. AACR, 1996, Abstract No. 2355, 345.
Duffy et al., "Effectiveness of *Bifidobacterium bifidum* in Mediating the Clinical Course of Murine Rotavirus Diarrhea," Pediatric Research, 1995, 35(6):690-695.
Fujimori et al., "The genus *Bifidobacterium* for cancer gene therapy," Curr. Opin. Drug Discov. Devel., 2002, 5(2):200-203.
Hirschowitz et al., "In Vivo Adenovirus-Mediated Gene Transfer of the *Escherichia coli* Cytosine Deaminase Gene to Human Colon Carcinoma-Derived Tumors Induces Chemosensitivity to 5-Flurocytosine," Human Gene Therapy, Aug. 1995, 6:1055-1063.
Huber et al., "In Vivo Antitumor Activyt of 5-Fluorocytosine on Human Colorectal Carcinoma Cells Genetically Modified to Express Cytosine Deaminase," Cancer Research, Oct. 1, 1993, 53:4619-4626.
Huber et al., "Metabolism of 5-fluorocytosine to 5-fluorouracil in human colorectal tumor cells transuced with the cytosine deaminase gene: Significant antitumor effects when only a small percentage of tumor cells express cytosine deaminase," Proc. Natl. Acad. Sci. USA, Aug. 1994, 91:8302-8306.
Ibrahim et al., "Inhibition of *Escherichia coli* by Bifidobacteria," Journal of Food Protection, Aug. 1993, 56(8):713-715.
Matsumura et al., "Construction of *Escherichia coli-Bifidobacterium longum* Shuttle Vector Transforming *B. longum* 105-A and 108-A," Biosci. Biotechnol. Biochem., 1997, 61(7):1211-1212.
Mitsuoka et al., "The Human Gastrointestinal Tract," Elsevier Applied Science, 1992, 69-114.
Mullen et al., "Tumors Expressing the Cytosine Deaminase Suicide Gene Can be Eliminated in Vivo with 5-Fluorocytosine and Induce Protective Immunity to Wild Type Tumor," Cancer Research, Mar. 15, 1994, 54:15031506.
Mullen et al., "Transfer of the bacterial gene for cytosine deaminase to mammalian cells confers lethal sensitivity to 5-fluorocytosine: A negative selection system," Proc. Natl. Acad. Sci. USA, Jan. 1992, 89:33-37.
Nishiyama et al., "Antineoplastic Effects in Rats of 5-Fluorocytosine in Combination with Cytosine Deaminase Capsules," Cancer Research, Apr. 1985, 45:1753-1761.
O'Donovan et al., "Pyrimidine Metabolism in Microorganisms," Bacteriological Reviews, Sep. 1970, 34:278-343.
Reddy et al., Inhibitory Effect of *Bifidobacterium longum* on Colon, Mammary, and Liver Carcinogenesis Induced by 2-Amino-3-methylimidazo[4,5-*f*]quinoline, a Food Mutagen,: Cancer Research, Sep. 1, 1993, 53:3914-3918.
Saaverdra et al., "Feeding of *Bifidobacterium bifidum* and *Streptococcus thermophilus* to infants in hospital for prevention of diarrhoea and shedding of rotavirus," Lancet, Oct. 15, 1994, 344:1046-1049.
Scardovi, Vittorio, "Genus *Bifidobacterium* Orla-Jensen 1924, 472$^{AL}$," Bergey's Manual of Systematic Bacteriology, vol. 2, eds. Sneath et al., 1986, 1418, 1426, 1434.
White et al., "Clinical, Cellular, and Molecular Factors That Contribute to Antifungal Drug Resistance," Clinical Microbiology Reviews, Apr. 1998, 11(2):382-402.
Yasui et al., "Enhancement of Immune Response in Peyer's Patch Cells Cultured with *Bifidobacterium breve*," J. Dairy Sci., 1991, 74:1187-1195.
Yazawa et al., "*Bifidobacterium longum* as a delivery system for cancer gene therapy: Selective localization and growth in hypoxic tumors," Cancer Gene Therapy, 2000, 7(2):269-274.

* cited by examiner

1. Wild-type Bifodobacterium longum
2. Bifodobacterium longum/pAV001-HU-eCD

5-FLUOROURACIL-RESISTANT BACTERIA AND METHOD FOR PRODUCTION THEREOF

CROSS-REFERENCE TO RELATED APPLICATIONS

This application claims the benefit of International Application Number PCT/JP2006/307102, filed on Apr. 4, 2006 under 35 USC §371, entitled, "5-Fluorouracil-Resistant Bacteria and Method for Production Thereof," which claims the benefit of Japanese Patent Application Number 2005-112557, filed on Apr. 8, 2005, both of which are hereby incorporated by reference.

TECHNICAL FIELD

The present invention relates to a method for producing cytosine deaminase (EC3.5.4.1; hereinafter referred to as CD)-expressing, 5-fluorouracil (hereafter referred to as 5-FU)-resistant microorganisms, which is useful as a therapeutic agents for solid tumors, can grow in anaerobic tumor tissues, can express CD, and has a resistance to 5-FU present at a concentration that is at least effective for antitumor activity. The present invention also relates to a 5-FU-resistant microorganism, a pharmaceutical composition containing the resistant microorganisms, and a therapeutic agent containing the resistant microorganism for treating solid tumors.

BACKGROUND ART

CD is an enzyme that deaminates cytosine to uracil (see for example, Non-Patent Document 1). CD plays an important role in microorganism metabolism. CD has been isolated from several different microorganisms, while it is not usually produced in mammalian cells (see for example, Non-Patent Document 2). Many of the bacteria and fungi that produce CD convert 5-fluorocytosine (hereafter referred to as 5-FC) to 5-FU, which is a highly toxic metabolite and is lethal to cells. 5-FU induces the generation of abnormal RNA and the inhibition of DNA synthesis. Antifungal action of 5-FC is due to this generation of abnormal RNA and inhibition of DNA synthesis by the action of 5-FU.

Specifically, 5-FC is taken up by fungal cells through cytosine permease and immediately converted to 5-FU in the cell by CD. Intercellular 5-FU is then converted through 5-FUMP to 5-FUDP by UMP-pyrophosphorylase. Subsequent phosphorylation pathway bifurcates into two branches, producing 5-FUTP through one pathway, and 5-FdUMP through the other pathway. Incorporation of 5-FUTP, instead of UTP, into RNA generates abnormal RNA and thus inhibits normal protein synthesis, resulting in the inhibition of fungal growth. Furthermore, 5-FdUMP works as a potent inhibitor of thymidylate synthase and inhibits DNA synthesis and nuclear division, leading to an antimicrobial effect.

However, because normal mammalian cells do not express significant amount of CD and thus 5-FC will not be deaminated into toxic metabolite 5-FU, 5-FC is nontoxic to the mammalian cells even at a concentration that shows potent antifungal activity. On the other hand, 5-FU is highly cytotoxic for mammalian cells as well and is widely used as an anticancer agent.

CD genes have been isolated and cloned from *Escherichia coli* and *Saccharomyces cerevisiae* (see for example, Non-Patent Documents 3 and 4). Many researchers have reported that introduction of a CD gene into a mammalian cell leads to decrease in selective sensitivity of the cell to 5-FC in vitro (see for example, Non-Patent Documents 3 and 5). It is also reported that tumor cells introduced with a CD gene by using a retroviral vector can be eliminated in vivo by systemic treatment of the animal with 5-FC (see for example, Non-Patent Documents 6-8). A replication-defective retroviral vector (see for example, Non-Patent Document 9) and a cationic liposome (see for example, Non-Patent Document 10) are also employed for the introduction of a CD gene respectively to human colon carcinoma cell line and mouse large cell lung cancer. These gene expressions in tumor cells grant the cells a sensitivity to 5-FC.

It is known that a resistance to 5-FC, which is used against fungal infections, for example by *Candida*, emerges easily (see for example, Non-Patent Document 11). Since the resistance to 5-FC could arise through loss or mutation of an enzyme relating to either the conversion of 5-FC to 5-FU or incorporation of 5-FU into RNA etc, there are theoretically a variety of mechanisms to obtain the resistance. Clinically, however, acquisition of resistance is most frequently accompanied with loss or decrease in activity of UMP-pyrophosphorylase in *Candida albicans*. It is also known that there is an obvious correlation between 5-FC sensitivity and enzymatic activity of UMP-pyrophosphorylase. Resistant strains that are deficient in cytosine permease or CD are also reported in *Candida glabrata* whose nuclear phase is monoploid.

On the other hand, *Bifidobacterium longum* is a Gram-positive anaerobic bacterium and has a genome with a high GC content (see for example, Non-Patent Document 12). This *Bifidobacterium longum* is nonpathogenic and constitutes a major part of normal microflora in the large intestine of humans and other animals (see for example, Non-Patent Document 13). *Bifidobacterium longum* is said to have health-promoting properties for their host, involving enhancement of the immune response (see for example, Non-Patent Document 14), inhibitory effect on carcinogenesis (see for example, Non-Patent Document 15), protection of the host against viral infections (see for example, Non-Patent Documents 16 and 17), and possibility of producing an antibacterial substance (see for example, Non-Patent Document 18). Some *Bifidobacterium* species are widely used throughout the world for preparing fermented dairy products.

Furthermore, plasmids for *Bifidobacterium* are expected to be applied to probiotics vectors and oral vaccine vectors against infectious diseases. For example, a transformation method comprising the steps of, (a) constructing a shuttle vector that is replicated in both *Bifidobacterium* sp. and *E. coli* using a plasmid originated from *Bifidobacterium* sp. and that originated from *E. coli*; (b) constructing a recombinant vector by inserting a target gene encoding a target protein into the shuttle vector; and (c) transforming the *Bifidobacterium* sp. used in the step (a) with the recombinant vector constructed in the step (b) is known (see for example, Patent Document 1). Furthermore, it has been revealed in recent reports that *Bifidobacterium longum* accumulates in hypoxic solid tumors after systemic application (see for example, Non-Patent Documents 19 and 20) and that recombinant plasmid pBLES100-S-eCD carrying *E. coli* codA fused to hup promoter from *Bifidobacterium longum* expresses CD in microorganisms (see for example, Patent Document 2, Non-Patent Documents 21 and 22). These findings support the effectiveness of recombinant *Bifidobacterium longum* for enzyme-prodrug therapy. pBLES100, which was used for construction of the recombinant plasmid pBLES100-S-eCD, is a shuttle vector constructed from *Bifidobacterium longum* BK51-derived pTB6 and *E. coli*-derived pBR322. The shuttle vector pBLES100 transformed *Bifidobacterium longum* with an efficiency of $2.2 \times 10^4$ transformants/μg DNA, and was stable in the cells in structure and segregation (see for example, Non-Patent Document 23). For the cloning of a foreign gene, however, even higher transformation efficiency is required because a plasmid having an unmodified DNA may be cleaved by a restriction enzyme in a microorganism during the transfection. Thus, the present inventors propose plasmids pAV001 and pBRASTA101, which can transform *Bifidobacterium longum* with 100 times or higher efficiency than pBLES100 (see for example, Non-Patent Document 24).

As mentioned above, 5-FU is highly cytotoxic to mammalian cells as well and widely used as an anticancer agent. However, for the administration of 5-FU by itself to a patient, it must be administered, for example, in such a way that its blood concentration is about 1 µg/ml or lower, or even when it is administered to exceed the blood concentration of 1 µg/ml, the time during which blood concentration exceeds 1 µg/ml should be about 1 hour at longest to avoid adverse effects. Under such situations, 5-FU cannot be said to fully exert its anticancer effect with the conventional methods. Under such circumstances, measures to treat tumors with high concentration of 5-FU while at the same time overcoming the adverse effects of 5-FU have been strongly desired.

[Patent Document 1] Published Japanese Translation of PCT International Application No. 2004-519236

[Patent Document 2] Japanese Laid-Open Patent Application No. 2002-97144

[Non-Patent Document 1] O'Donovan et al., Bact. Rev. 34:278 (1970)

[Non-Patent Document 2] Nishiyama et al., Cancer Res. 45:1753 (1985)

[Non-Patent Document 3] Austin et al., Pharmacol. 43:380 (1992)

[Non-Patent Document 4] Anderson et al., Arch. Microbiol. 152:115 (1989)

[Non-Patent Document 5] Mullen et al., Proc. Natl. Acad. Sci. USA 89:33 (1992)

[Non-Patent Document 6] Huber et al., Cancer Res. 53:4619 (1993)

[Non-Patent Document 7] Mullen et al., Cancer Res. 54: 1503 (1994)

[Non-Patent Document 8] Huber et al., Proc. Natl. Acad. Sci. USA 91:8302 (1994)

[Non-Patent Document 9] Hirschowitz et al., Human Gene Ther. 6:1055 (1995)

[Non-Patent Document 10] Davis et al., Proc. AACR Abstract No. 2355, p 345 (1996)

[Non-Patent Document 11] Clin. Microbiol. Rev. 11:382-402. 1998

[Non-Patent Document 12] Scardovi, Bergey's Manual of Systematic Bacteriology vol 2, eds. Sneath et al., pp. 1418-1434 (1986)

[Non-Patent Document 13] Mitsuoka, Elsevier Applied Science, pp 69-114 (1992)

[Non-Patent Document 14] Yasui et al. J. Dairy Sci., 74, 1187-1195 (1991)

[Non-Patent Document 15] Reddy et al., Cancer Res., 53, 3914-3918 (1993)

[Non-Patent Document 16] Duffy et al., Pediatr. Res., 35, 690-695 (1994)

[Non-Patent Document 17] Saaverdra et al., Lancet., 344, 1046-1049 (1994)

[Non-Patent Document 18] Ibrahim et al., J. Food Prot., 56, 713-715 (1993)

[Non-Patent Document 19] Yazawa et al. Cancer Gene Ther., 7, 269-274 (2000)

[Non-Patent Document 20] Yazawa et al. Breast Cancer Res. Treat., 66, 165-170 (2001)

[Non-Patent Document 21] Nakamura et al., Biosci. Biotechnol. Biochem., 66, 2362-2366 (2002)

[Non-Patent Document 22] Fujimori et al., Curr. Opin. Drug Discov. Devel., 5, 200-203 (2002)

[Non-Patent Document 23] Matsumura et al., Biosci. Biotechnol. Biochem., 61, 1211-1212 (1997)

[Non-Patent Document 24] Tanaka et al., Biosci Biotechnol Biochem.; 69(2):422-425 (2005, February)

DISCLOSURE OF THE INVENTION

Object to be Solved by the Invention

An enzyme/pro-drug therapy using CD/5-FC is a therapy widely used in animal experiments, clinical tests, etc. In such an enzyme-prodrug therapy, if 5-FU resistance of the CD gene introduced cells (microorganisms) is enhanced, it is expected that the therapeutic effect of the enzyme/pro-drug therapy using CD/5-FC will be significantly improved because such cells (microorganisms) will not be eradicated by 5-FU and therefore have a good survival rate. An object of the present invention is to provide a method for producing such CD-expressing, 5-FU-resistant microorganisms useful as a therapeutic agents for the enzyme/pro-drug therapy, being capable of expressing CD, and having a resistance to 5-FU at a concentration that is at least effective for antitumor activity. Another object of the invention is to provide a 5-FU-resistant microorganism that enables the treatment of tumors with high concentration of 5-FU while at the same time overcoming the adverse effects of 5-FU, to provide a pharmaceutical composition containing the resistant microorganism, and a therapeutic agent of solid tumors containing the resistant microorganisms Means to Solve the Object The present inventors have studied earnestly to solve the objects described above and found out that a 5-FU-resistant microorganism maintaining CD activity can be produced by subculture or acclimation culture of a CD-expressing microorganism, which is transformed with a CD gene, in the presence of 5-FC. Specifically, when CD-expressing microorganisms are cultured in a culture medium supplemented with a specified amount of 5-FC, 5-FC is gradually converted to 5-FU by enzymatic activity of CD that has expressed along with the proliferation of the CD-expressing microorganism. Therefore, although the specified amount of 5-FC is added, it initially acts as a low concentration of 5-FU, avoiding the eradication of the CD-expressing microorganisms. Due to this gradual increase of 5-FU, CD-expressing, 5-FU-resistant microorganisms, which has acquired a resistance, can be selectively cultured. Alternatively, the present inventors found out that a CD-expressing, 5-FU-resistant microorganism can be also produced by subculture or acclimation culture of CD non-expressing microorganisms in the presence of 5-FU to produce a 5-FU-resistant microorganism and transforming the resultant 5-FU-resistant microorganisms by introducing a CD gene. Furthermore, the present inventors found out that treatment of a tumor with a high concentration of 5-FU while overcoming the adverse effects of 5-FU can be achieved with the use of the 5-FU-resistant microorganism obtained by such methods, and have completed the present invention.

Namely, the present invention relates to [1] a method for producing a cytosine deaminase-expressing, 5-fluorouracil-resistant microorganism which can grow in anaerobic tumor tissues, can express cytosine deaminase, and has a resistance to 5-fluorouracil at a concentration that is at least effective for antitumor activity, wherein a subculture or acclimation culture of a cytosine deaminase-expressing microorganism which can grow in anaerobic tumor tissues is performed in the presence of 5-fluorocytosine; [2] the method for producing a resistant microorganism according to [1], wherein the cytosine deaminase-expressing microorganism which can grow in anaerobic tumor tissues is a cytosine deaminase-expressing microorganism produced by transforming a microorganism which does not express cytosine deaminase and can grow in anaerobic tumor tissues by introducing a cytosine deaminase gene; [3] the method for producing a resistant microorganism according to [1] or [2], wherein the subculture or acclimation culture is performed with a medium supplemented with 2 to 5000 μg/ml of 5-fluorocytosine; [4] the method for producing a resistant microorganism according to any one of [1] to [3], wherein the cytosine deaminase-expressing microorganism which can grow in anaerobic tumor tissues is a bacterium which can grow in anaerobic tumor tissues and expresses cytosine deaminase; [5] the method for producing a resistant microorganism according to [4], wherein the bacterium which can grow in anaerobic tumor tissues and expresses cytosine deaminase is an enteric bacterium expressing cytosine deaminase; [6] the method for producing a resistant microorganism according to [5], wherein the enteric bacterium expressing cytosine deaminase is a bacterium belonging to the genus *Bifidobacterium* expressing cytosine deaminase; [7] the method for producing a resistant microorganism according to [6], wherein the bacterium belonging to the genus *Bifidobacterium* expressing cytosine deaminase is *Bifidobacterium longum*, *Bifidobacterium breve*, or *Bifidobacterium infantis* expressing cytosine deaminase; [8] the method for producing a resistant microorganism according to [7], wherein the bacterium belonging to the genus *Bifidobacterium* expressing cytosine deaminase is *Bifidobacterium longum* expressing cytosine deaminase; [9] a method for producing a cytosine deaminase-expressing, 5-fluorouracil-resistant microorganism which can grow in anaerobic tumor tissues, can express cytosine deaminase, and has a resistance to 5-fluorouracil at a concentration that is at least effective for antitumor activity, wherein the method comprises the steps of (1) performing a subculture or acclimation culture, in the presence of 5-fluorouracil, of a microorganism which can grow in anaerobic tumor tissues and does not express cytosine deaminase to generate a 5-fluorouracil-resistant microorganism; and (2) transforming the 5-fluorouracil-resistant microorganism by introducing a cytosine deaminase gene; [10] the method for producing a resistant microorganism according to [9], wherein the subculture or acclimation culture is performed with a medium supplemented with 1 to 100 μg/ml of 5-fluorouracil; [11] the method for producing a resistant microorganism according to [9] or [10], wherein the microorganism which can grow in anaerobic tumor tissues and does not express cytosine deaminase is a bacterium which can grow in anaerobic tumor tissues and does not express cytosine deaminase; [12] the method for producing a resistant microorganism according to [11], wherein the bacterium which can grow in anaerobic tumor tissues and does not express cytosine deaminase is an enteric bacterium which does not express cytosine deaminase; [13] the method for producing a resistant microorganism according to [12], wherein the enteric bacterium which does not express cytosine deaminase is a bacterium belonging to the genus *Bifidobacterium* which does not express cytosine deaminase; [14] the method for producing a resistant microorganism according to [13], wherein the bacterium belonging to the genus *Bifidobacterium* which does not express cytosine deaminase is *Bifidobacterium longum*, *Bifidobacterium breve*, or *Bifidobacterium infantis* which does not express cytosine deaminase; [15] the method for producing a resistant microorganism according to [14], wherein the bacterium belonging to the genus *Bifidobacterium* which does not express cytosine deaminase is *Bifidobacterium longum* which does not express cytosine deaminase; [16] a cytosine deaminase-expressing, 5-fluorouracil-resistant microorganism which can grow in anaerobic tumor tissues, can express cytosine deaminase, and has a resistance to 5-fluorouracil at a concentration that is at least effective for antitumor activity, wherein the cytosine deaminase-expressing, 5-fluorouracil-resistant microorganism is produced by the method according to any one of [1] to [15]; [17] the cytosine deaminase-expressing, 5-fluorouracil-resistant microorganism which can grow in anaerobic tumor tissues, express cytosine deaminase, and grow in a medium supplemented with at least 2 μg/ml of 5-fluorocytosine or 1 μg/ml of 5-fluorouracil; [18] cytosine deaminase-expressing, 5-fluorouracil-resistant microorganism according to [16] or [17], wherein the cytosine deaminase-expressing, 5-fluorouracil-resistant microorganism is a cytosine deaminase-expressing, 5-fluorouracil-resistant bacterium; [19] the cytosine deaminase-expressing, 5-fluorouracil-resistant microorganism according to [18], wherein the cytosine deaminase-expressing, 5-fluorouracil-resistant bacterium is a cytosine deaminase-expressing, 5-fluorouracil-resistant enteric bacterium; [20] the cytosine deaminase-expressing, 5-fluorouracil-resistant microorganism according to [19], wherein the cytosine deaminase-expressing, 5-fluorouracil-resistant enteric bacterium is a cytosine deaminase-expressing, 5-fluorouracil-resistant bacterium belonging to the genus *Bifidobacterium*; [21] the cytosine deaminase-expressing, 5-fluorouracil-resistant microorganism according to [20], wherein the cytosine deaminase-expressing, 5-fluorouracil-resistant bacterium belonging to the genus *Bifidobacterium* is a cytosine deaminase-expressing, 5-fluorouracil-resistant *Bifidobacterium longum*, *Bifidobacterium breve*, or *Bifidobacterium infantis*; [22] the cytosine deaminase-expressing, 5-fluorouracil-resistant microorganism according to [20], wherein the cytosine deaminase-expressing, 5-fluorouracil-resistant bacterium belonging to the genus *Bifidobacterium* is a cytosine deaminase-expressing, 5-fluorouracil-resistant *Bifidobacterium longum*; [23] the cytosine deaminase-expressing, 5-fluorouracil-resistant microorganism according to [22], wherein the cytosine deaminase-expressing, 5-fluorouracil-resistant *Bifidobacterium longum* is a cytosine deaminase-expressing, 5-fluorouracil-resistant *Bifidobacterium longum* 105-A strain carrying the plasmid pBLES100-S-eCD or a mutant plasmid thereof; [24] the cytosine deaminase-expressing, 5-fluorouracil-resistant microorganism according to [23], wherein the cytosine deaminase-expressing, 5-fluorouracil-resistant *Bifidobacterium longum* is a cytosine deaminase-expressing, 5-fluorouracil-resistant *Bifidobacterium longum* 105-A strain carrying the plasmid pAV001-HU-eCD or a mutant plasmid thereof; [25] the cytosine deaminase-expressing, 5-fluorouracil-resistant microorganism according to [21], wherein the cytosine deaminase-expressing, 5-fluorouracil-resistant *Bifidobacterium breve* is a cytosine deaminase-expressing, 5-fluorouracil-resistant *Bifidobacterium breve* type strain carrying the plasmid pAV001-HU-eCD or a mutant plasmid thereof; [26] the cytosine deaminase-expressing, 5-fluorouracil-resistant microorganism according to [21], wherein the cytosine deaminase-expressing, 5-fluorouracil-resistant *Bifidobacterium breve* is a cytosine deaminase-expressing, 5-fluorouracil-resistant *Bifidobacterium breve* aS-1 strain carrying the plasmid pAV001-HU-eCD or a mutant plasmid thereof; [27]

the cytosine deaminase-expressing, 5-fluorouracil-resistant microorganism according to [21], wherein the cytosine deaminase-expressing, 5-fluorouracil-resistant *Bifidobacterium breve* is a cytosine deaminase-expressing, 5-fluorouracil-resistant *Bifidobacterium breve* I-53-8W strain carrying the plasmid pAV001-HU-eCD or a mutant plasmid thereof; [28] the cytosine deaminase-expressing, 5-fluorouracil-resistant microorganism according to [21], wherein the cytosine deaminase-expressing, 5-fluorouracil-resistant *Bifidobacterium infantis* is a cytosine deaminase-expressing, 5-fluorouracil-resistant *Bifidobacterium infantis* type strain carrying the plasmid pAV001-HU-eCD or a mutant plasmid thereof; [29] the cytosine deaminase-expressing, 5-fluorouracil-resistant microorganism according to [21], wherein the cytosine deaminase-expressing, 5-fluorouracil-resistant *Bifidobacterium infantis* is a cytosine deaminase-expressing, 5-fluorouracil-resistant *Bifidobacterium infantis* I-10-5 strain carrying the plasmid pAV001-HU-eCD or a mutant plasmid thereof; [30] a pharmaceutical composition comprising a cytosine deaminase-expressing, 5-fluorouracil-resistant microorganisms according to any one of [16] to [29]; [31] the pharmaceutical composition according to [30], combined with 5-fluorocytosine; [32] the pharmaceutical composition according to [30] or [31], further combined with lactulose; [33] a therapeutic agent for treating solid tumors consisting of a combination of a cytosine deaminase-expressing, 5-fluorouracil-resistant microorganism in an amount sufficient for expressing cytosine deaminase in an amount that can convert 5-fluorocytosine to a therapeutically effective amount of 5-flucrouracil, and 5-fluorocytosine in an amount to be converted to the therapeutically effective amount of 5-flucrouracil, wherein the cytosine deaminase-expressing, 5-fluorouracil-resistant microorganism is a cytosine deaminase-expressing, 5-fluorouracil-resistant microorganism according to any of any one of [16] to [29]; and [34] the therapeutic agent for treating solid tumors according to [33], in combination with lactulose.

BEST MODE OF CARRYING OUT THE INVENTION

Figure 1:
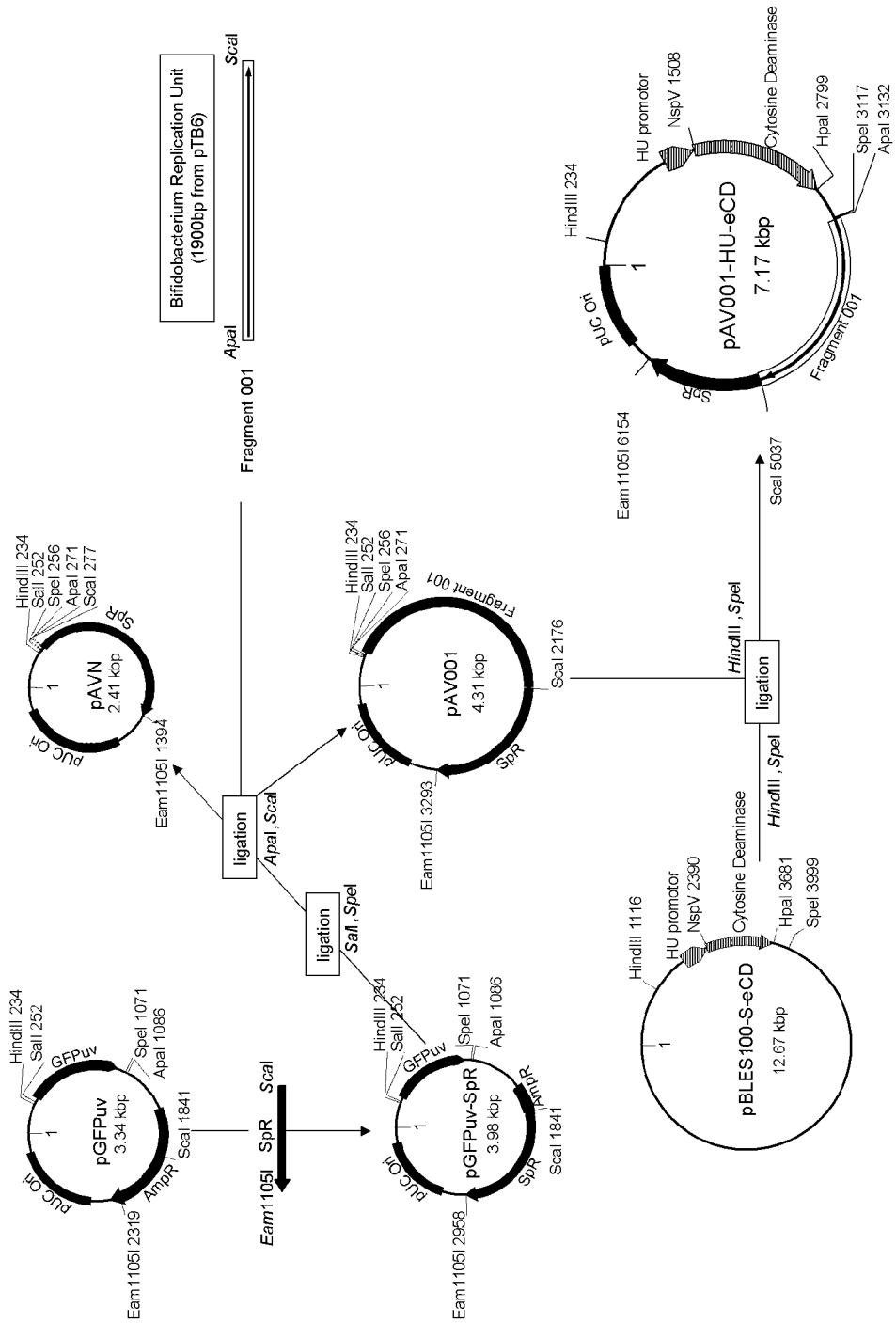
FIG. 1 It is a diagram showing a process of producing a *Bifidobacterium-E. coli* shuttle vector pAV001 and a CD expression shuttle vector pAV001-HU-eCD.

A method for producing a 5-FU-resistant microorganism of the present invention is not particularly limited as long as the method is the following (A) or (B): (A) a method comprising subculture or acclimation culture of a CD-expressing microorganism which can grow in anaerobic tumor tissues, in the presence of 5-FC; or (B) a method comprising the steps of (1) performing subculture or acclimation culture of a microorganism which can grow in anaerobic tumor tissues and does not express CD, in the presence of 5-FU, to produce a 5-FU-resistant microorganism, and (2) transforming the 5-FU-resistant microorganism by introducing a CD gene.

A CD-expressing microorganism which can grow in anaerobic tumor tissues in the above method (A) is not particularly limited as long as it is a microorganism which expresses CD and can grow in anaerobic tumor tissues. The microorganism may be a microorganism isolated from nature or may be a recombinant microorganism produced by transforming a microorganism which can grow in anaerobic tumor tissues and does not express CD by introducing a CD gene.

A microorganism which can grow in anaerobic tumor tissues and does not express CD used in the above method (B) is not particularly limited as long as it is a microorganism which does not express CD and can grow in anaerobic tumor tissues.

Examples of microorganisms used in the producing methods of the present invention, which can grow in anaerobic tumor tissues include bacteria and fungi. Specific examples of such bacteria include enteric bacteria belonging to the genera such as *Bifidobacterium, Clostridium, Lactobacillus, Streptococcus, Peptococcus, Enterococcus, Bacteroides*, and *Eubacterium*. Among these, the bacteria belonging to the genus *Bifidobacterium* are preferred.

Specific examples of the bacteria belonging to the genus *Bifidobacterium* include *Bifidobacterium longum, Bifidobacterium breve, Bifidobacterium adolescentis, Bifidobacterium lactentis, Bifidobacterium bifidum, Bifidobacterium pseudolongum, Bifidobacterium thermophirum, Bifidobacterium infantis*, and *Bifidobacterium animalis*. Among these, *Bifidobacterium longum, Bifidobacterium breve, Bifidobacterium adolescentis, Bifidobacterium bifidum*, and *Bifidobacterium infantis*, known to inhabit in the human intestines regardless of age, are preferable as a host bacterium, and *Bifidobacterium longum* is more preferred. All these bacteria are commercially available or can be obtained easily from depository institutions. For example, *Bifidobacterium longum* ATCC-15707, *Bifidobacterium bifidum* ATCC-11863, or *Bifidobacterium infantis* ATCC-15697 can be used.

Exemplary strains of *Bifidobacterium longum* include, without limitation, *Bifidobacterium longum* 105-A, *Bifidobacterium longum* aE-194b, *Bifidobacterium longum* bs-601, and *Bifidobacterium longum* M101-2. Among these, *Bifidobacterium longum* 105-A can be preferably exemplified.

Further, exemplary strains of *Bifidobacterium breve* include, without limitation, *Bifidobacterium breve* type strain (JCM1192), *Bifidobacterium breve* aS-1, and *Bifidobacterium breve* I-53-8W.

Further, exemplary strains of *Bifidobacterium infantis* include, without limitation, *Bifidobacterium infantis* type stain (JCM1222) and *Bifidobacterium infantis* 1-10-5.

Further, exemplary strains of *Bifidobacterium* lactentis include, without limitation, *Bifidobacterium* lactentis type strain (JCM1220).

Subculture or acclimation culture in the presence of 5-FC in the method (A) can be carried out by performing anaerobic culture at 37° C. in a culture medium (liquid medium or agar plate) suitable for growth and proliferation of bacteria or fungi, said medium supplemented with 5-FC at a concentration within the range, for example, from 2 to 5000 μg/ml, preferably from 2 to 2000 μg/ml.

When the microorganisms are cultured in a culture medium supplemented with 5-FC, 5-FC is gradually converted to 5-FU by CD, expressed along with the proliferation of the microorganism. Thus, 5-FU acts in low concentration at first, avoiding the eradication of the cultured microorganism with the gradual increase of 5-FU concentration. Therefore, only the microorganisms that have obtained a resistance can be selectively cultured. In this manner, the 5-FU-resistant microorganism of the present invention can be collected reproducibly.

Subculture or acclimation culture in the presence of 5-FU in the above method (B) can be carried out by performing anaerobic culture at 37° C. in a culture medium (liquid medium or agar plate) suitable for growth and proliferation of bacteria or fungi, said medium supplemented with 5-FU at a concentration within the range, for example, from 1 to 100 μg/ml, preferably from 2 to 100 μg/ml. In this manner, 5-FU-resistant microorganism can be collected reproducibly.

A CD-expressing microorganism transformed by the introduction of a CD gene, and a CD expression vector and a transformant used for preparing a microorganism transformed by the introduction of a gene that grants the microorganism an ability to grow in an anaerobic condition can be prepared according to the methods described in commercially available experiment manuals such as Idenshi Manyuaru (Gene Manual (Kodansha)); Idenshi Sosa Jikkenhou (Methods for Experiments in Gene Manipulation (ed., Yasutaka Takagi, Kodansha)); Molecular Cloning (Cold Spring Harbor Laboratory (1982)); Molecular Cloning, 2nd ed. (Cold Spring Harbor Laboratory (1989)); Methods in Enzymology, 194 (1991); and Jikken Igaku bessatsu, Kobo niyoru Idenshi Jikkenhou (Gene Experiments Using Yeasts, Experimental Medicine Suppl (Yodosha (1994))). Preferably, an expression vector suitable for a host microorganism should be used.

For a CD-encoding DNA, for example, DNA isolated from a plasmid pAdex1 CSCD (Riken Gene Bank, EDB No. 1591), which contains a DNA encoding an *E. coli*-derived CD, or a plasmid pMK116, which also contains a DNA encoding the *E. coli*-derived CD, can be used (D. A. Mead et al., Protein Engineering 1:67-74 (1986)).

In particular, examples of CD expression vectors for the bacteria belonging to the genus *Bifidobacterium* preferably include a recombinant plasmid pBLES100-S-eCD carrying an *E. coli* codA inserted at downstream of *Bifidobacterium longum* hup promoter (see Patent Document 1 and Non-Patent Document 21) pAV001-HU-eCD, which was made by improving the pBLES100-S-eCD and capable of transforming *Bifidobacterium longum* and *Bifidobacterium breve*, and mutants of these plasmids.

A mutant of the plasmid pBLES100-S-eCD refers to a mutant of nucleic acid sequence of pBLES100-S-eCD-derived plasmid, which can be used in the same way as pBLES100-S-eCD in the present invention. Similarly, the mutants of the plasmid pAV001-HU-eCD refer to mutants of nucleic acid sequence of pAV001-HU-eCD-derived plasmid, wherein the mutants can be used in the same way as pAV001-HU-eCD in the present invention.

A CD-expressing, 5-FU-resistant microorganism of the present invention is not particularly limited as long as it can grow in an anaerobic tumor tissue, can express CD, and has a resistance to 5-FU at a concentration that is at least effective for antitumor activity. Although the effective concentration of 5-FU for antitumor activity varies depending on subject tissues, patients and the like, the concentration from at least 0.05 to 0.1 μg/ml can be exemplified.

Additionally, an instruction of a commercially available 5-FU formulation (for injection) describes a continuous intravenous injection of the 5-FU formulation was performed to a patient of advanced gastric cancer so that blood concentration of 5-FU becomes approximately 0.6 μg/ml.

For a more specific 5-FU resistance of a CD-expressing, 5-FU-resistant microorganism of the present invention, it is an ability to grow when anaerobically cultured at 37° C. in a culture medium (liquid medium or agar plate) containing at least 1 to 2000 μg/ml, preferably 2 to 2000 μg/ml of 5-FU.

Furthermore, when the 5-FU resistance of a CD-expressing, 5-FU-resistant microorganism of the present invention is expressed specifically in relation to the 5-FC concentration, it is an ability to grow when anaerobically cultured at 37° C. in a culture medium (liquid medium or agar plate) containing 2 to 5000 μg/ml, preferably 3 to 5000 μg/ml of 5-FC.

Although the 5-FU resistance of a CD-expressing, 5-FU-resistant microorganism of the present invention may be an ability to grow when anaerobically cultured at 37° C. in a culture medium (liquid medium or agar plate) containing 5-FU at a concentration within the above described range, or an ability to grow when anaerobically cultured at 37° C. in a culture medium (liquid medium or agar plate) containing 5-FC at the concentration within the above described range, the desired resistance of the CD-expressing, 5-FU-resistant microorganism of the present invention is an ability to grow in a medium containing at least 1 μg/ml or more of 5-fluorouracil or an ability to grow in a medium containing at least 2 μg/ml or more of 5-fluorocytosine.

There is no limitation for a method for producing the CD-expressing, 5-FU-resistant microorganism of the present invention, and the method may be isolation from nature or may employ the above-described methods for producing a microorganism of the present invention. Namely, a CD-expressing, 5-FU-resistant microorganism of the present invention may be a microorganism isolated from nature or a recombinant microorganism produced by the above-described methods for producing a microorganism of the present invention.

A CD-expressing, 5-FU-resistant microorganism of the present invention is not particularly limited as long as it is a bacterium or fungus which can grow in anaerobic tumor tissues, can express CD, and has a resistance to 5-FU at a concentration that is at least effective for antitumor activity. However, a bacterium having these properties is preferred, and an enteric bacterium having these properties is more preferred. For enteric bacteria, bacteria belonging to the genera *Bifidobacterium*, *Clostridium*, *Lactobacillus*, *Streptococcus*, *Peptococcus*, *Enterococcus*, *Bacteroides*, *Eubacterium* or the like can be preferably exemplified. Among these, bacteria belonging to the genus *Bifidobacterium* can be more preferably exemplified.

Specific examples of bacteria belonging to the genus *Bifidobacterium* include *Bifidobacterium longum*, *Bifidobacterium breve*, *Bifidobacterium adolescentis*, *Bifidobacterium lactentis*, *Bifidobacterium bifidum*, *Bifidobacterium pseudolongum*, *Bifidobacterium thermophirum*, *Bifidobacterium infantis*, and *Bifidobacterium animalis*. Among these, *Bifidobacterium longum*, *Bifidobacterium breve*, *Bifidobacterium adolescentis*, *Bifidobacterium bifidum*, and *Bifidobacterium infantis*, which are known to inhabit in human intestines regardless of age, are preferable as a host bacterium, and *Bifidobacterium longum*, is more preferable. All these bacteria are commercially available or can be obtained easily from depository institutions. For example, *Bifidobacterium longum* ATCC-15707, *Bifidobacterium bifidum* ATCC-11863, and *Bifidobacterium infantis* ATCC-15697 can be used.

Exemplary strains of *Bifidobacterium longum* include, without limitation, *Bifidobacterium longum* 105-A, *Bifidobacterium longum* aE-194b, *Bifidobacterium longum* bs-601, and *Bifidobacterium longum* M101-2. Among these, *Bifidobacterium longum* 105-A can be preferably exemplified.

Further, exemplary strains of *Bifidobacterium breve* include, without limitation, *Bifidobacterium breve* type strain (JCM1192), *Bifidobacterium breve* aS-1, and *Bifidobacterium breve* I-53-8W.

Further, exemplary strains of *Bifidobacterium infantis* include, without limitation, *Bifidobacterium infantis* type stain (JCM1222) and *Bifidobacterium infantis* I-10-5

Further, exemplary strains of *Bifidobacterium lactentis* include, without limitation, *Bifidobacterium lactentis* type strain (JCM1220).

More specifically, preferable examples of bacteria having the above properties and belonging to the genus *Bifidobacterium* include a CD-expressing, 5-FU-resistant *Bifidobacterium longum* 105-A strain carrying the plasmid pBLES100-S-eCD or a mutant plasmid thereof (a *Bifidobacterium longum* 105A strain transformed with the plasmid pBLES100-S-eCD or a mutant plasmid thereof); a CD-expressing, 5-FU-resistant *Bifidobacterium longum* 105-A strain carrying the plasmid pAV001-HU-eCD or a mutant plasmid thereof; a CD-expressing, 5-FU-resistant *Bifidobacterium breve* type strain carrying the plasmid pAV001-HU-eCD or a mutant plasmid thereof; a CD-expressing, 5-FU-resistant *Bifidobacterium breve* aS-1 strain carrying the plasmid pAV001-HU-eCD or a mutant plasmid thereof; a CD-expressing, 5-FU-resistant *Bifidobacterium breve* I-53-8W strain carrying the plasmid pAV001-HU-eCD or a mutant plasmid thereof; a CD-expressing 5-FU-resistant *Bifidobacterium infantis* type strain carrying the plasmid pAV001-HU-eCD or a mutant plasmid thereof; and a CD-expressing, 5-FU-resistant *Bifidobacterium infantis* I-10-5 strain carrying the plasmid pAV001-HU-eCD or a mutant plasmid thereof.

A pharmaceutical composition of the present invention is not particularly limited as long as it contains the CD-expressing, 5-FU-resistant microorganism of the present invention. Furthermore, the pharmaceutical composition of the present invention can contain one or more kinds of a CD-expressing, 5-FU-resistant microorganisms of the present invention.

The dosage of a CD-expressing, 5-FU-resistant microorganisms contained in a pharmaceutical composition of the present invention is not particularly limited as long as it is a sufficient amount for the expression of CD in an amount that can convert 5-FC to a therapeutically effective amount of 5-FU. However, preferably the dosage should be as low as possible.

A pharmaceutical compositions of the present invention may contain any optional component other than the CD-expressing, 5-FU-resistant microorganism of the present invention as long as it does not hinder the effect of the present invention. Such optional components include, for example, pharmaceutically acceptable carriers, excipients and diluents. The pharmaceutical compositions of the present invention are used in combination with 5-FC in an amount that can be converted to an effective amount of 5-FU by a CD-expressing, 5-FU-resistant microorganism of the present invention. Although 5-FC may be contained in the pharmaceutical compositions of the present invention, it is preferable to use another pharmaceutical composition containing 5-FC in combination with the pharmaceutical composition of the present invention. Furthermore, the pharmaceutical compositions of the present invention may be combined with sugars that can promote the proliferation of the CD-expressing, 5-FU-resistant microorganisms of the present invention. Examples of such sugars include lactulose.

The term "combination of X and Y (X combined with Y)" used in the present invention includes both cases that X and Y are in different forms and that X and Y are in the same form (e.g. a form containing X and Y). In the case that X and Y are in different forms, both X and Y may further contain other components.

When a pharmaceutical composition of the present invention is administered to a patient, the CD-expressing, 5-FU-resistant microorganism of the present invention grows in tumor tissues. If 5-FC is administered while the resistant microorganisms exist in the tumor, 5-FC will be converted to 5-FU by the action of CD in the tumor. The resulting 5-FU can kill the tumor cells. Because the CD-expressing, 5-FU-resistant microorganisms of the present invention can survive in the presence of 5-FU at a concentration that can kill tumor cells, the enzymatic activity of CD can be maintained. Thus, excellent antitumor drugs containing the CD-expressing, 5-FU-resistant microorganisms of the present invention as an active ingredient can be obtained. Furthermore, the CD-expressing, 5-FU-resistant microorganisms of the present invention cannot survive in the parts other than anaerobic tumor tissues in which the CD-expressing, 5-FU-resistant microorganisms can grow. Thus, 5-FC will not be converted to 5-FU there and the systemic side-effects of 5-FU can be restricted in dramatically low level compared with the administration of 5-FU by itself. Furthermore, antitumor effects of the therapeutic agents of the present invention for treating solid tumors have high specificity to tumors. Thus, dramatically high levels of 5-FU can be achieved in tumors compared with the administration of 5-FU by itself, consequently yielding exceptionally excellent antitumor effects.

For a dosage form of a pharmaceutical composition of the present invention, liquid formulation and solid formulation containing a CD-expressing, 5-FU-resistant microorganism of the present invention can be exemplified. The liquid formulation can be prepared by purifying the culture solution of the CD-expressing, 5-FU-resistant microorganism of the present invention, optionally adding adequate physiological saline or fluid replacement, or pharmaceutical additives, and filling it in an ampule or a vial etc. For a preparation of a solid formulation, a liquid formulation may be added with an adequate protectant, filled in an ampule or a vial etc. and freeze-dried or L-dried. Alternatively, the liquid formulation may be added with an adequate protectant, freeze-dried or L-dried, and filled in an ampule or a vial. As for an administration method of a pharmaceutical composition of the present invention, parental administration is preferred and subcutaneous injection, intravenous injection, localized injection, and intraventricular administration can be exemplified. Among these, intravenous injection is the most preferable.

A pharmaceutical composition of the present invention is used in combination with 5-FC. The pharmaceutical composition of the present invention and 5-FC may be administered either in a same administration method or different methods, and may be administered either simultaneously or separately. Preferably, the administration of 5-FC should be after that of a pharmaceutical composition of the present invention to allow the CD-expressing, 5-FU-resistant microorganisms of the present invention to grow sufficiently in tumor tissues.

The dosage of 5-FC used in combination with the pharmaceutical compositions of the present invention is not particularly limited as long as it is a sufficient amount for 5-FC to be converted to therapeutically effective amount of 5-FU by the CD-expressing, 5-FU-resistant microorganisms of the present invention. However, preferably it should be as low as possible. The dosage can be selected appropriately from, for example, the range from 5 to 200 mg/kg Furthermore, a pharmaceutical composition of the present invention can be used in combination with sugars that promote the proliferation of the CD-expressing, 5-FU-resistant microorganisms of the present invention. Examples of such sugars include lactulose. Such sugars may be administered as a component of a pharmaceutical composition of the present invention, or as a different pharmaceutical composition, either simultaneously or separately with a pharmaceutical composition of the present invention.

The present invention will be explained more specifically by referring to Examples below, but the technological scope of the present invention is not limited to these exemplifications.

Reference Example 1

Production of CD-Expressing *Bifidobacterium longum*

The CD-expressing *Bifidobacterium longum* was produced as described in Japanese patent application No. 2004-339677.

1. Construction of Shuttle Vector pAV001
(Plasmid Construction)

A sequence that includes gene encoding spectinomycin adenyltransferase (AAD cassette) of *Enterococcus faecalis* was amplified by PCR from pBLES100, which is a shuttle vector of *Bifidobacterium longum* and *E. coli* (see Patent Document 2 and Non-Patent Document 23), and subcloned into pCR-BluntII-TOPO vector (Invitrogen) to prepare pCR-TOPO-ScaI-AAD-Eam1105I. ScaI and Eam1105I restriction sites were added to forward and reverse primers, respectively.

As shown in FIG. 1, a cloning vector pGFPuv (DEFINITION: Cloning vector pGFPuv. ACCESSION: U62636; VERSION: U62636.1 GI: 1490528) purchased from Invitrogen is composed of GFPuv gene with Multi-Cloning sites (MCS) at the both ends of the gene, an ampicillin resistance gene, and an *E. coli* plasmid replication origin.

The ampicillin resistance gene in the pGFPuv was excised by cleaving with restriction enzymes Eam1105I and ScaI to produce a long fragment. Similarly, pCRTOPO-ScaI-AAD-Eam1105I was cleaved with Eam1105I and ScaI to produce a fragment (approximately 1100 bp) containing an AAD cassette. These two fragments were ligated by T4 DNA ligase to produce pGFPuv-SpR. The addition of spectinomycin resistance property and loss of ampicillin resistance in the pGFPuv-SpR are respectively confirmed in *E. coli*.

pGFPuv-SpR was digested with restriction enzymes SalI (located in the multi-cloning site upstream of GFPuv gene) and SpeI (located in the multi-cloning site downstream of GFPuv gene) to produce pAVN plasmid that is deprived of GFPuv gene.

A sequence of approximately 1900 bp containing RepB, SDO, DDO, AT-rich repeats, and DnaA-binding motifs was identified as a plasmid replication unit of *Bifidobacterium longum* from the complete nucleotide sequence information of the *Bifidobacterium longum*-derived plasmid pTB6. The approximately 1900-bp sequence that contains the plasmid replication unit of *Bifidobacterium longum* was amplified by PCR from pTB6 and subcloned into pCR-BluntII-TOPO vector to produce pCRTOPO-ApaI-1900-ScaI. Restriction enzyme recognition sites of ApaI and ScaI were added to forward and reverse primers respectively.

A long fragment yielded by digesting pAVN with restriction enzymes ApaI and ScaI (approximately 2400 bp) and a short fragment yielded by similarly digesting pCRTOPO-APAI-1900-ScaI (approximately 1900 bp) were ligated together by using T4 DNA ligase to produce a *Bifidobacterium longum-E. coli* shuttle vector pAV001 (approximately 4300 bp).

2. CD Gene Expression Vector pAV001-HU-eCD
(Construction of Expression Vector)

Next, pBLES100-S-eCD was cleaved with restriction enzymes Hind III and SpeI to extract an approximately 2900-bp fragment containing an HU gene promoter, an E-coli-derived CD gene, and an HU gene terminator. Similarly, the shuttle vector pAV001 was cleaved with restriction enzymes HindIII and SpeI at the restriction sites in the multi-cloning site. The obtained long fragment and the above approximately 2900-bp fragment were ligated by using T4 DNA ligase to produce pAV001-HU-eCD (approximately 7100 bp).

3. Introduction of the CD Gene Expression Vector pAV001-HU-eCD into the Genus *Bifidobacterium*

Wild-type *Bifidobacterium longum* was cultured in MRS medium at 37° C. under anaerobic conditions and the resulting culture medium was centrifuged to isolate the bacterial cells, which were then suspended in an appropriate buffer to prepare a bacterial suspension. Next, the cytosine deaminase gene expression vector pAV001-HU-eCD was introduced into the cells in the bacterial suspension by electroporation method as described in Non-Patent Document 23. Transformed recombinant *Bifidobacterium longum* (*Bifidobacterium longum*/pAV001-HU-eCD) was selected based on colony formation on an agar medium containing the antibiotic spectinomycin.

(Expression of Cytosine Deaminase in Recombinant *Bifidobacterium longum*)

Figure 2:
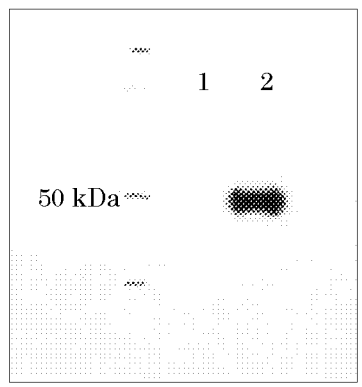
FIG. 2 It is a figure showing the comparison result of the expression level of CD protein between a wild-type *Bifidobacterium longum* and *Bifidobacterium*/pAV001-HU-eCD.

*Bifidobacterium longum*/pAV001-HU-eCD and wild-type *Bifidobacterium longum* were subcultured respectively in MRS medium containing the antibiotic spectinomycin at 37° C. under anaerobic conditions for two or more days. The bacterial cells were separated ($1 \times 10^9$ CFU) from the culture medium by centrifugation, which is then sonicated and followed by extraction of intracellular proteins respectively. The extracted proteins were separated by SDS-polyacrylamide gel electrophoresis. The expression of a cytosine deaminase protein was confirmed by western blotting using rabbit anti-cytosine deaminase monoclonal antibody (Sawaday Technology) as the primary antibody and horseradish peroxidase-conjugated anti-rabbit immunoglobulin G (Santa Cruz Biotechnology, Inc) as the secondary antibody. The signals were visualized by ECL system and detected as luminescence signals with Fluo-S-MAX cooled CCD camera (BIO-RAD). Signals were detected from *Bifidobacterium longum*/pAV001-HU-eCD, showing the expression of cytosine deaminase proteins, while no signal was detected from wild-type *Bifidobacterium longum*, showing the nonexpression of cytosine deaminase (see FIG. 2).

(Measurement of Enzymatic Activity of Cytosine Deaminase (5-FC→5-FU Conversion Activity) in *Bifidobacterium longum*/pAV001-HU-eCD)

Figure 3:
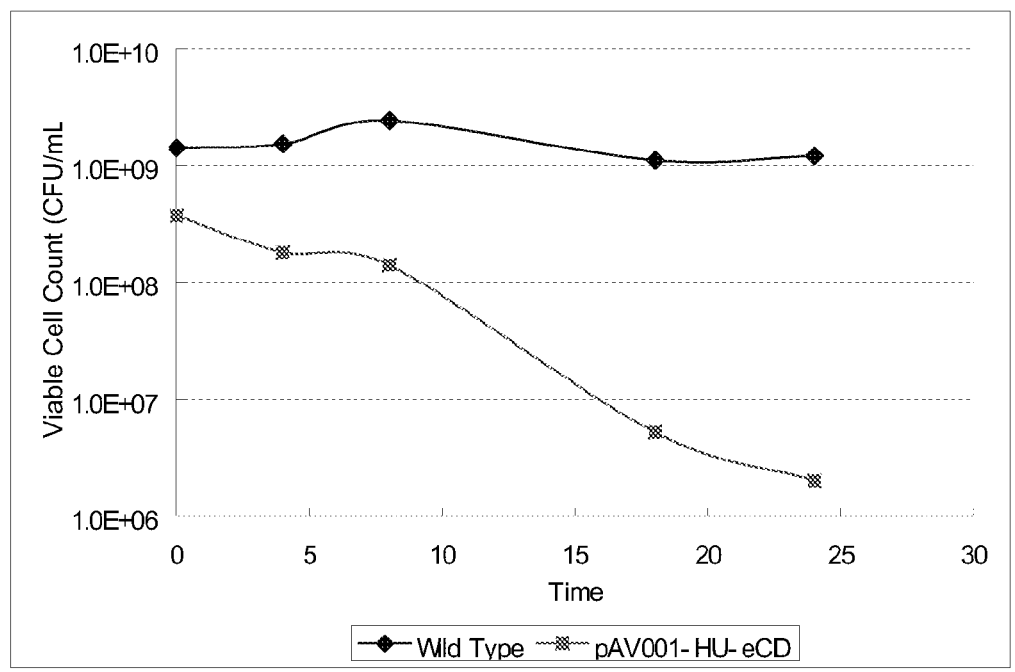
FIG. 3 It is a graph showing the profile of cell count versus time obtained from the comparison of CD enzymatic activity (comparison of activity for conversion of 5-FC to 5-FU) between a wild-type *Bifidobacterium longum* and *Bifidobacterium*/pAV001-HU-eCD.
Figure 4:
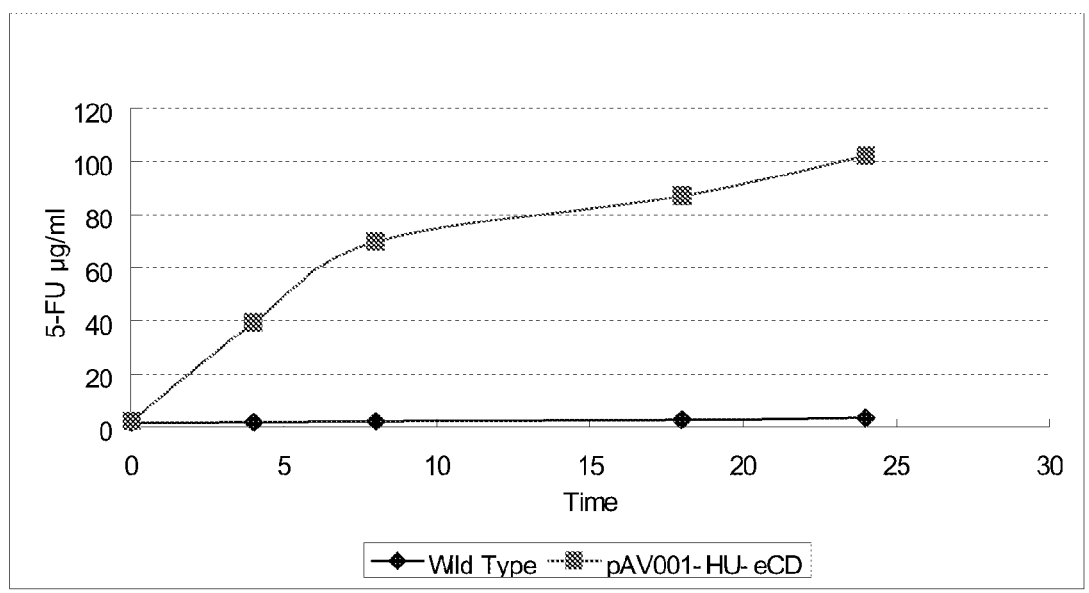
FIG. 4 It is a graph showing the 5-FU concentrations obtained from the comparison of CD enzymatic activity (comparison of activity for conversion of 5-FC to 5-FU) between a wild-type *Bifidobacterium longum* and *Bifidobacterium*/pAV001-HU-eCD.

*Bifidobacterium longum*/pAV001-HU-eCD and wild-type *Bifidobacterium longum* were respectively subcultured in MRS medium containing the antibiotic spectinomycin at 37° C. under anaerobic conditions for two or more days. The bacterial cells were separated from the culture solution by centrifugation ($2 \times 10^9$ CFU), resuspended in 4.5 ml of MRS medium, and 0.5 ml of 5-FC (20 mg/mL) was added to the final concentration of 2 mg/mL, and then cultured at 37° C. under anaerobic conditions. After 0, 4, 8, 18, and 24 hours, the culture solutions were centrifuged and the supernatants were collected, of which the bacterial cells were removed. The converted 5-FU concentration in the supernatants were measured by gas chromatography analysis (5-FU GC-MS methods, BML). The profile of viable cell count versus time is shown in FIG. 3. 5-FU concentrations are shown in FIG. 4. As a result, In *Bifidobacterium longum*/pAV001-HU-eCD, 5-FU was detected in 39.2 μg/mL after 4 hours and in 102.1 μg/mL after 24 hours, while extremely low amount of 5-FU was detected in wild-type *Bifidobacterium*.

Example 1

5-FU-Resistant Microorganisms of *Bifidobacterium longum*/pAV001-HU-eCD

*Bifidobacterium longum*/pAV001-HU-eCD obtained in Reference Example 1 was inoculated into 5 mL of MRS medium containing the antibiotic spectinomycin and 50 μg/mL of 5-FC, followed by anaerobic culture at 37° C. for 72 hours. Then, 1 mL of the culture medium was similarly inoculated into 9 mL of MRS medium containing the antibiotic spectinomycin and 50 μg/mL of 5-FC, and cultured for 24 hours under the same culture conditions. This inoculation step was repeated three rounds to produce the 5-FU-resistant *Bifidobacterium longum*/pAV001-HU-eCD. Next, the 5-FU-resistant growth of the produced 5-FU-resistant *Bifidobacterium longum*/pAV001-HU-eCD was confirmed by inoculating into MRS medium containing 20 μg/mL of 5-FU and the antibiotic spectinomycin and culturing for 24 hours under the same culture conditions as above. Then, the bacteria were suspended with glycerol and stored at −80° C. as glycerol stocks. The stored bacteria sample and wild-type *Bifidobacterium longum* were inoculated respectively into MRS media containing 250 μg/mL of 5-FU and the antibiotic spectinomycin and growths thereof were compared. The growth of bacteria from the stored sample was observed on the following day, indicating the maintenance of 5-FU resistance, while the wild type did not grow. Viable cell counts of the post-culture bacterial culture were determined by plate count method. The viable cell count was 2 to $3\times10^9$ CFU/mL for the bacterial culture of the stored sample, while that of the wild type was below the limit of detection (below $10^3$ CFU/mL).

[Measurement of 5-FU Concentration, to which the 5-FU-Resistant *Bifidobacterium longum* is Resistant]

5-FU-resistant *Bifidobacterium longum*/pAV001-HU-eCD obtained in Example 1 and wild-type *Bifidobacterium longum* were respectively subcultured in MRS medium at 37° C. under anaerobic conditions for two or more days. The cultured solution were diluted with anaerobic diluent, spread onto BL agar media containing 0, 25, 50, 100, 250, 500, 1000, or 2000 μg/mL of 5-FU, and cultured anaerobically at 37° C. for 2 to 3 days. Then, the viable cell counts were determined. The experiments using 5-FU-free BL agar media were performed in quintuplicate and the other experiments using 5-FU containing BL agar media were performed in triplicate. The results are shown in Tables 1 (5-FU-resistant *Bifidobacterium longum*/pAV001-HU-eCD) and 2 (wild-type *Bifidobacterium longum*). As shown in Table 1, 5-FU-resistant *Bifidobacterium longum*/pAV001-HU-eCD has a resistance to 5-FU, the concentration of which is at least 2000 μg/mL. On the contrary, the wild-type *Bifidobacterium longum* did not grow in the presence of 5-FU at a concentration of at least 25 μg/mL or higher (Table 2).

TABLE 1

5-FU-resistant *Bifidobacterium longum*/pAV001-HU-eCD

| 5-FU Content (μg/mL) | 1 | 2 | 3 | 4 | 5 | Average | sd | CV (%) | Growth Rate (%) |
|---|---|---|---|---|---|---|---|---|---|
| 0 | 144 | 126 | 175 | 138 | 165 | 149.6 | 20.0 | 13.4 | |
| 25 | 116 | 148 | 124 | | | 129.3 | 16.7 | 12.9 | 86% |
| 50 | 129 | 129 | 128 | | | 128.7 | 0.6 | 0.4 | 86% |
| 100 | 118 | 139 | 107 | | | 121.3 | 16.3 | 13.4 | 81% |
| 250 | 100 | 107 | 114 | | | 107.0 | 7.0 | 6.5 | 72% |
| 500 | 175 | 116 | 153 | | | 148.0 | 29.8 | 20.1 | 99% |
| 1000 | 168 | 123 | 147 | | | 146.0 | 22.5 | 15.4 | 98% |
| 2000 | 127 | 128 | 124 | | | 126.3 | 2.1 | 1.6 | 84% | sd: standard deviation
CV: coefficient of variation

TABLE 2

Wild-type *Bifidobacterium longum*

| 5-FU Content (μg/mL) | 1 | 2 | 3 | 4 | 5 | Average | sd | CV (%) | Growth Rate (%) |
|---|---|---|---|---|---|---|---|---|---|
| 0 | 108 | 117 | 104 | 126 | 137 | 118.4 | 13.43 | 11.34 | |
| 25 | 0 | 0 | 0 | | | 0.0 | 0.0 | — | 0% |
| 50 | 0 | 0 | 0 | | | 0.0 | 0.0 | — | 0% |
| 100 | 0 | 0 | 0 | | | 0.0 | 0.0 | — | 0% |
| 250 | 0 | 0 | 0 | | | 0.0 | 0.0 | — | 0% |
| 500 | 0 | 0 | 0 | | | 0.0 | 0.0 | — | 0% |
| 1000 | 0 | 0 | 0 | | | 0.0 | 0.0 | — | 0% |
| 2000 | 0 | 0 | 0 | | | 0.0 | 0.0 | — | 0% | sd: standard deviation
CV: coefficient of variation

[Maintenance of 5-FU-Resistant Trait in 5-FU-Resistant *Bifidobacterium longum*]

5-FU-resistant *Bifidobacterium longum*/pAV001-HU-eCD obtained in Example 1 was subcultured anaerobically in MRS medium containing the antibiotic spectinomycin at 37° C. for two or more days. 5 μL of the cultured solution was inoculated into 5 mL of MRS medium that is free of the antibiotic spectinomycin, and cultured anaerobically at 37° C. for 24 hours. The cultured solution was subcultured similarly for 30 days continually. After the 30-day continual subculture, the cultured solution was diluted with an anaerobic diluent, spread onto a BL agar medium containing 250 μg/mL of 5-FU or a 5-FU-free BL agar medium, and cultured anaerobically at 37° C. for 2 to 3 days. Then the viable cell counts were determined. The experiments were performed in quintuplicate. The results are shown in Table 3. As known from Table 3, the 5-FU-resistant trait of 5-FU-resistant *Bifidobacterium longum* was maintained at least after the 30-day continual subculture.

TABLE 3

| 5-FU Content (μg/mL) | 1 | 2 | 3 | 4 | 5 | Average | sd | CV (%) | Growth Rate (%) |
|---|---|---|---|---|---|---|---|---|---|
| 0 | 146 | 197 | 134 | 153 | 149 | 155.8 | 24.10 | 15.47 | |
| 250 | 166 | 152 | 124 | 137 | 194 | 154.6 | 27.09 | 17.52 | 99% | sd: standard deviation
CV: coefficient of variation

[Culture of 5-FU-Resistant *Bifidobacterium longum* and 5-FU Non-Resistant *Bifidobacterium longum* in Liquid Media Containing 5-FC]

The *Bifidobacterium longum*/pAV001-HU-eCD obtained in Reference Example 1 (5-FU non-resistant *Bifidobacterium longum*) and the *Bifidobacterium longum*/pAV001-HU-eCD obtained in Example 1 (5-FU-resistant *Bifidobacterium longum*) were respectively subcultured under anaerobic conditions at 37° C. in MRS media containing the antibiotic spectinomycin for two or more days. Then, 50 μL of each of the cultured solution was inoculated into MRS media containing 5-FC at the concentration of 5, 25, 50, 100, 250, or 500 μg/mL and cultured at 37° C. under anaerobic conditions for 24 hours. After the culture, the growth of each bacteria was determined by measuring the turbidity of the post-culture solution (OD=600 nm) (Table 4). The growth of the 5-FU non-resistant *Bifidobacterium longum* was remarkably inhibited in media containing 50 μg/mL or more of 5-FC. In contrast, 5-FU-resistant *Bifidobacterium longum* grew for all 5-FC concentrations.

TABLE 4

| Turbidity Measurement | | 5-FC Content (μg/mL) | | | | | |
|---|---|---|---|---|---|---|---|
| (OD = 600 nm) | | 5 | 25 | 50 | 100 | 250 | 500 |
| Reference Example 1 | 5-FU non-resistant *Bifidobacterium longum* | 6.43 | 4.29 | 1.92 | 0.68 | 0.19 | 0.09 |
| Example 1 | 5-FU-resistant *Bifidobacterium longum* | 5.73 | 5.38 | 4.11 | 5.41 | 5.15 | 4.29 |

Example 2

5-FU-Resistant Bacteria of *Bifidobacterium longum*/pAV001-HU-eCD Produced by Using 5-FU Containing Media

*Bifidobacterium longum* was inoculated into 5 mL of MRS media containing 1, 5, 10, 50, 100, or 500 μg/mL of 5-FU and cultured anaerobically at 37° C. for one to five days. Turbidities were measured (OD=600 nm) for each culture to examine the growth (Table 5). For the medium containing 500 μg/mL of 5-FU, no growth was observed even after 5 days and resistant bacterium strain could not be obtained. For other media, in which the growth was observed, 1 mL of each of the post-culture media was inoculated into 9 mL of MRS media containing the same concentration of 5-FU, and cultured for 24 hours under the same culture conditions. This inoculation step was repeated three rounds to produce 5-FU-resistant *Bifidobacterium longum* in each 5-FU concentration. Next, each 5-FU-resistant *Bifidobacterium longum* was inoculated into MRS media. Each of post-culture solution was inoculated into MRS media containing 250 μg/mL of 5-FU. After 24 hours of incubation, turbidities were measured (OD=600 nm) to determine the growth (Table 6). As a result, the 5-FU-resistant *Bifidobacterium longum* produced from media containing 1 to 100 μg/mL of 5-FU have the same level of 5-FU resistance as the 5-FU-resistant strain obtained in Example 1.

TABLE 5

| | 5-FU concentration used for grant of resistance (μg/mL) | | | | | | |
|---|---|---|---|---|---|---|---|
| OD = 600 nm | 1 | 5 | 10 | 50 | 100 | 500 | 1000 |
| Culture days 1 | 4.94 | 0.22 | 0.09 | 0.00 | −0.05 | −0.05 | −0.06 |
| 2 | 4.94 | 4.39 | 5.51 | 0.44 | 0.01 | −0.07 | −0.08 |
| 3 | 4.94 | 4.39 | 5.51 | 4.99 | 0.12 | −0.08 | −0.06 |
| 4 | 4.94 | 4.39 | 5.51 | 4.99 | 5.88 | 0.07 | 0.01 |
| 5 | 4.94 | 4.39 | 5.51 | 4.99 | 5.88 | 0.08 | 0.02 |

TABLE 6

| | 5-FU concentration used for grant of resistance (μg/mL) | | | | | | |
|---|---|---|---|---|---|---|---|
| | 1 | 5 | 10 | 50 | 100 | 500 | 1000 |
| Growth rate of 5-FU-resistant strains | 20% | 55% | 62% | 90% | 95% | 0% | 0% |

Example 3

5-FU-resistant strains obtained in Example 2 were transformed by the same method as Reference Example 1 and the expression of cytosine deaminase was confirmed. The produced cytosine deaminase-expressing, 5-FU-resistant strains have a 5-FU resistance similarly as the 5-FU-resistant strains obtained in Example 1. Furthermore, the 5-FU resistance was maintained for at least 7 days or more.

Example 4

5-FU-resistant strains were produced from *Bifidobacterium breve*, *Bifidobacterium infantis*, and *Bifidobacterium lactentis* by the same method as Example 1. A list of 5-FU-resistant *Bifidobacterium* strains is shown in Table 7 below.

TABLE 7

List of resistance-required strains produced by the same method as the example 1

| Species | Strain | Introduced Plasmid |
| --- | --- | --- |
| B. longum | 105-A | pBLES100-S-eCD |
| B. longum | 105-A | pAV001-HU-eCD |
| B. longum | aE-194b | pAV001-HU-eCD |
| B. longum | bs-601 | pAV001-HU-eCD |
| B. longum | M101-2 | pAV001-HU-eCD |
| B. lactentis | Type strain JCM1220 | pAV001-HU-eCD |
| B. infantis | Type strain JCM1222 | pAV001-HU-eCD |
| B. infantis | I-10-5 | pAV001-HU-eCD |
| B. breve | Type strain JCM1192 | pAV001-HU-eCD |
| B. breve | aS-1 | pAV001-HU-eCD |
| B. breve | I-53-8W | pAV001-HU-eCD |

INDUSTRIAL APPLICABILITY

The present invention makes it possible to easily produce 5-FU-resistant microorganisms such as bacteria belonging to the genus *Bifidobacterium* maintaining CD activity and showing 5-FU resistance, which are very useful for an enzyme/pro-drug therapy employing CD/5-FC. For example, after administration of the bacteria belonging to the genus *Bifidobacterium* maintaining CD activity and showing 5-FU resistance to a cancer patient, the bacteria belonging to the genus *Bifidobacterium* proliferate in tumors. If 5-FC is administered orally while the bacteria exist in tumors, the 5-FC will be absorbed through intestinal tract and converted to 5-FU by the CD activity in tumors and the resultant 5-FU can kill the tumor cells. However, the 5-FU-resistant bacteria belonging to the genus *Bifidobacterium* can survive in the presence of 5-FU at a concentration that is high enough to kill tumor cells, and can maintain the CD enzyme activity. Therefore, an excellent antitumor drug that contains the bacteria belonging to the genus *Bifidobacterium* as an active ingredient can be obtained.

5-FC will not be converted to 5-FU in places other than tumors where a CD-expressing, 5-fluorouracil-resistant microorganism of the present invention proliferates. Thus, the adverse effects of 5-FU can be remarkably suppressed in low level, compared with the administration of 5-FU by itself. Furthermore, a therapeutic agent for treating solid tumors in accordance with the present invention has antitumor effects of high specificity to tumors. Therefore the agent can achieve remarkably high concentration of 5-FU in tumors, resulting to excellent antitumor effects

The invention claimed is:

1. A cytosine deaminase-expressing, 5-fluorouracil-resistant microorganism which can grow in anaerobic tumor tissues, can express cytosine deaminase, and has a resistance to 5-fluorouracil at a concentration that is at least effective for antitumor activity, wherein the cytosine deaminase-expressing, 5-fluorouracil-resistant microorganism has a viability such that it can grow in a medium supplemented with at least 2 µg/ml of 5-fluorocytosine or 1 µg/ml of 5-fluorouracil.

2. The cytosine deaminase-expressing, 5-fluorouracil-resistant microorganism of claim 1, wherein the microorganism is produced by (A): performing a subculture or acclimation culture of a cytosine deaminase-expressing microorganism which can grow in anaerobic tumor tissues, in the presence of 5-fluorocytosine, wherein the subculture or acclimation culture is performed with a medium supplemented with 2 to 5000 µg/ml of 5-fluorocytosine; or (B) performing a subculture or acclimation culture, in the presence of 5-fluorouracil, of a microorganism which can grow in anaerobic tumor tissues and does not express cytosine deaminase, to generate a 5-fluorouracil-resistant microorganism; and transforming the 5-fluorouracil-resistant microorganism by introducing a cytosine deaminase gene, wherein the subculture or acclimation culture is performed with a medium supplemented with 1 to 100 µg/ml of 5-fluorouracil.

3. The cytosine deaminase-expressing, 5-fluorouracil-resistant microorganism according to claim 1, wherein the cytosine deaminase-expressing, 5-fluorouracil-resistant microorganism is a cytosine deaminase-expressing, 5-fluorouracil-resistant bacterium.

4. The cytosine deaminase-expressing, 5-fluorouracil-resistant microorganism according to claim 3, wherein the cytosine deaminase-expressing, 5-fluorouracil-resistant bacterium is a cytosine deaminase-expressing, 5-fluorouracil-resistant enteric bacterium.

5. The cytosine deaminase-expressing, 5-fluorouracil-resistant microorganism according to claim 4, wherein the cytosine deaminase-expressing, 5-fluorouracil-resistant enteric bacterium is a cytosine deaminase-expressing, 5-fluorouracil-resistant bacterium belonging to the genus *Bifidobacterium*.

6. The cytosine deaminase-expressing, 5-fluorouracil-resistant microorganism according to claim 5, wherein the cytosine deaminase-expressing, 5-fluorouracil-resistant bacterium belonging to the genus *Bifidobacterium* is a cytosine deaminase-expressing, 5-fluorouracil-resistant *Bifidobacterium longum*, *Bifidobacterium breve*, or *Bifidobacterium infantis*.

7. The cytosine deaminase-expressing, 5-fluorouracil-resistant microorganism according to claim 6, wherein the cytosine deaminase-expressing, 5-fluorouracil-resistant bacterium belonging to the genus *Bifidobacterium* is a cytosine deaminase-expressing, 5-fluorouracil-resistant *Bifidobacterium longum*.

8. The cytosine deaminase-expressing, 5-fluorouracil-resistant microorganism according to claim 7, wherein the cytosine deaminase-expressing, 5-fluorouracil-resistant *Bifidobacterium longum* is a cytosine deaminase-expressing, 5-fluorouracil-resistant *Bifidobacterium longum* 105-A strain carrying the plasmid pBLES100-S-eCD.

9. The cytosine deaminase-expressing, 5-fluorouracil-resistant microorganism according to claim 7, wherein the cytosine deaminase-expressing, 5-fluorouracil-resistant *Bifidobacterium longum* is a cytosine deaminase-expressing, 5-fluorouracil-resistant *Bifidobacterium longum* 105-A strain carrying the plasmid pAV001-HU-eCD.

10. The cytosine deaminase-expressing, 5-fluorouracil-resistant microorganism according to claim 1, wherein the growth rate after culturing 2 to 3 days in a medium supplemented with at least 25 µg/ml of 5-fluorouracil has a viability of about 70% or more.

11. A pharmaceutical composition comprising a cytosine deaminase expressing, 5-fluorouracil-resistant microorganisms according to claim 1.

12. The pharmaceutical composition according to claim 11, combined with 5-fluorocytosine.

13. The pharmaceutical composition according to claim 12, further combined with lactulose.

14. A therapeutic agent for treating solid tumors comprising a combination of a cytosine deaminase-expressing, 5-fluorouracil-resistant microorganism in an amount sufficient for expressing cytosine deaminase in an amount that can convert 5-fluorocytosine to a therapeutically effective amount of 5-fluorouracil, and 5-fluorocytosine in an amount to be converted to the therapeutically effective amount of 5 fluorouracil, wherein the cytosine deaminase-expressing, 5-fluorouracil-resistant microorganism is a cytosine deaminase-expressing, 5-fluorouracil-resistant microorganism according to claim 1.

15. The therapeutic agent for treating solid tumors according to claim 14, further combined with lactulose.

16. A pharmaceutical composition comprising a microorganism that expresses cytosine deaminase, grows in anaerobic tissues, and is resistant to 5-fluorouracil at a concentration of at least 1 µg/ml of 5-fluorouracil.

17. The pharmaceutical composition according to claim 16, wherein the cytosine deaminase-expressing, 5-fluorouracil-resistant microorganism is a cytosine deaminase-expressing, 5-fluorouracil-resistant bacterium.

18. The pharmaceutical composition according to claim 17, wherein the cytosine deaminase-expressing, 5-fluorouracil-resistant bacterium is a cytosine deaminase-expressing, 5-fluorouracil-resistant enteric bacterium.

19. The pharmaceutical composition according to claim 18, wherein the cytosine deaminase-expressing, 5-fluorouracil-resistant enteric bacterium is a cytosine deaminase-expressing, 5-fluorouracil-resistant bacterium belonging to the genus *Bifidobacterium*.

20. The pharmaceutical composition according to claim 19, wherein the cytosine deaminase-expressing, 5-fluorouracil-resistant bacterium belonging to the genus *Bifidobacterium* is a cytosine deaminase-expressing, 5-fluorouracil-resistant *Bifidobacterium longum, Bifidobacterium breve*, or *Bifidobacterium infantis*.

21. The pharmaceutical composition according to claim 20, wherein the cytosine deaminase-expressing, 5-fluorouracil-resistant bacterium belonging to the genus *Bifidobacterium* is a cytosine deaminase-expressing, 5-fluorouracil-resistant *Bifidobacterium longum*.

22. The pharmaceutical composition according to claim 21, wherein the cytosine deaminase-expressing, 5-fluorouracil-resistant *Bifidobacterium longum* is a cytosine deaminase-expressing, 5-fluorouracil-resistant *Bifidobacterium longum* 105-A strain carrying the plasmid pBLES 100-S-eCD or a mutant plasmid thereof.

23. The pharmaceutical composition according to claim 21, wherein the cytosine deaminase-expressing, 5-fluorouracil-resistant *Bifidobacterium longum* is a cytosine deaminase-expressing, 5-fluorouracil-resistant *Bifidobacterium longum* 105-A strain carrying the plasmid pAV001-HU-eCD or a mutant plasmid thereof.

24. The pharmaceutical composition according to claim 16, combined with 5-fluorocytosine.

25. The pharmaceutical composition according to claim 24, further combined with lactulose.

* * * * *

UNITED STATES PATENT AND TRADEMARK OFFICE
CERTIFICATE OF CORRECTION

| | | |
|---|---|---|
| PATENT NO. | : 8,734,779 B2 | Page 1 of 1 |
| APPLICATION NO. | : 11/910880 | |
| DATED | : May 27, 2014 | |
| INVENTOR(S) | : Hamaji et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,614 days.

Signed and Sealed this
Seventh Day of June, 2016

Michelle K. Lee
*Director of the United States Patent and Trademark Office*